United States Patent
Pichara et al.

(10) Patent No.: US 12,205,488 B2
(45) Date of Patent: Jan. 21, 2025

(54) SYSTEMS AND METHODS TO MIMIC TARGET FOOD ITEMS USING ARTIFICIAL INTELLIGENCE

(71) Applicant: NotCo Delaware, LLC, Santiago (CL)

(72) Inventors: Karim Pichara, San Francisco, CA (US); Pablo Zamora, Melipilla (CL); Matias Muchnick, NY, NY (US); Orlando Vasquez, Santiago (CL)

(73) Assignee: Notco Delaware, LLC, Santiago (CL)

( * ) Notice: Subject to any disclaimer, the term of this patent is extended or adjusted under 35 U.S.C. 154(b) by 771 days.

(21) Appl. No.: 17/479,770

(22) Filed: Sep. 20, 2021

(65) Prior Publication Data
US 2022/0005376 A1 Jan. 6, 2022

Related U.S. Application Data

(63) Continuation of application No. 16/416,095, filed on May 17, 2019, now Pat. No. 11,164,478.

(51) Int. Cl.
*G09B 19/00* (2006.01)
*G01N 33/02* (2006.01)
(Continued)

(52) U.S. Cl.
CPC ....... *G09B 19/0092* (2013.01); *G01N 33/025* (2013.01); *G01N 33/12* (2013.01);
(Continued)

(58) Field of Classification Search
CPC ............ G09B 19/0092; G06F 16/9035; G01N 33/025; G01N 33/12; G06N 3/04; G06N 3/08
See application file for complete search history.

(56) References Cited

U.S. PATENT DOCUMENTS

| 5,305,076 A | 4/1994 | Inoue et al. |
| 8,044,354 B2 | 10/2011 | Werner et al. |

(Continued)

FOREIGN PATENT DOCUMENTS

| CN | 106844738 A | 6/2017 |
| CN | 108509601 A | 4/2018 |

(Continued)

OTHER PUBLICATIONS

Hahladakis et al., "An Overview of Chemical Additives Present in Plastics: Migration, Release, Fate and Environmental Impact During Their Use, Disposal and Recycling", Journal of Hazardous Materials 344 (2018), pp. 179-199.
(Continued)

*Primary Examiner* — David E Choi
(74) *Attorney, Agent, or Firm* — Haverstock & Owens, A Law Corporation

(57) ABSTRACT

Systems and methods to mimic a target food item using artificial intelligence are disclosed. The system can learn from open source and proprietary databases. A prediction model can be trained using features of the source ingredients to match those of the given target food item. A formula comprising a combination of most relevant source ingredients and their proportions can be determined using the trained prediction model. A set of existing recipes can be used as a dataset to train a recurrent neural network (RNN) and/or other suitable models. The RNN can be used to determine a recipe to mimic the target food item. The recipe may comprise a cooking process for the set of ingredients in the formula and can be cooked by a chef. The recipe may be further modified as necessary based on human feedback on sensorial descriptors.

20 Claims, 11 Drawing Sheets

(51) Int. Cl.
  *G01N 33/12* (2006.01)
  *G06F 16/9035* (2019.01)
  *G06N 3/04* (2023.01)
  *G06N 3/08* (2023.01)

(52) U.S. Cl.
  CPC .......... *G06F 16/9035* (2019.01); *G06N 3/04* (2013.01); *G06N 3/08* (2013.01)

(56) References Cited

U.S. PATENT DOCUMENTS

| | | |
|---|---|---|
| 8,419,433 B2 | 4/2013 | Do et al. |
| 8,647,121 B1 | 2/2014 | Witlin |
| 8,775,341 B1 | 7/2014 | Commons |
| 9,513,167 B2 | 12/2016 | Hargreaves et al. |
| 9,519,620 B1 | 12/2016 | Pinel et al. |
| 9,841,897 B2 | 12/2017 | Palmer et al. |
| 10,325,181 B2 | 6/2019 | Xu |
| 10,515,715 B1 | 12/2019 | Pappas et al. |
| 10,915,818 B1 | 2/2021 | Patel et al. |
| 10,957,424 B1 | 3/2021 | Navon et al. |
| 10,962,473 B1 | 3/2021 | O'Hara et al. |
| 10,970,621 B1 | 4/2021 | Pichara et al. |
| 10,984,145 B1 | 4/2021 | Hutchinson et al. |
| 10,993,465 B2 | 5/2021 | Pichara et al. |
| 11,048,976 B2 | 6/2021 | Tian et al. |
| 11,164,069 B1 | 11/2021 | Korsunsky et al. |
| 11,164,478 B2 | 11/2021 | Pichara et al. |
| 11,348,664 B1 | 5/2022 | Kaneko et al. |
| 11,373,107 B1 | 6/2022 | Clavero et al. |
| 11,404,144 B1 | 8/2022 | Kang et al. |
| 11,514,350 B1 | 11/2022 | Kaneko et al. |
| 11,631,034 B2 * | 4/2023 | Pichara ............... G06F 18/2431 426/534 |
| 11,644,416 B2 * | 5/2023 | O'Hara .................... G06N 5/04 702/28 |
| 11,685,928 B2 * | 6/2023 | Lanquar ............. C12N 15/8257 800/312 |
| 11,741,383 B2 * | 8/2023 | Clavero ................. G06N 3/088 706/50 |
| 11,819,041 B2 * | 11/2023 | Varadan ................ A23L 13/422 |
| 11,840,717 B2 * | 12/2023 | Lanquar ......... C12Y 304/21009 |
| 11,982,661 B1 * | 5/2024 | Estay ...................... G06N 3/045 |
| 12,029,225 B2 * | 7/2024 | Hazell ................... A23L 29/206 |
| 2002/0184167 A1 | 12/2002 | McClanahan |
| 2003/0157725 A1 | 8/2003 | Franzen et al. |
| 2004/0153250 A1 | 8/2004 | Hurst et al. |
| 2005/0143936 A1 | 6/2005 | Laughlin et al. |
| 2007/0139667 A1 | 6/2007 | Russell et al. |
| 2009/0055247 A1 | 2/2009 | Jackson |
| 2011/0020518 A1 | 1/2011 | Delort et al. |
| 2012/0082362 A1 | 4/2012 | Diem et al. |
| 2012/0328178 A1 | 12/2012 | Remiszewski et al. |
| 2013/0149679 A1 | 6/2013 | Tokuda et al. |
| 2013/0221222 A1 | 8/2013 | Baiz et al. |
| 2013/0222406 A1 | 8/2013 | Wolfe et al. |
| 2015/0199608 A1 | 7/2015 | Pinel et al. |
| 2016/0025569 A1 | 1/2016 | Hargreaves et al. |
| 2016/0110584 A1 | 4/2016 | Remiszewski et al. |
| 2016/0358043 A1 | 12/2016 | Mu |
| 2017/0116517 A1 | 4/2017 | Chee |
| 2017/0139902 A1 | 5/2017 | Byron |
| 2017/0220558 A1 | 8/2017 | Pinel et al. |
| 2017/0238590 A1 | 8/2017 | Bansal-Mutalik et al. |
| 2017/0345185 A1 | 11/2017 | Byron et al. |
| 2018/0101784 A1 | 4/2018 | Rolfe et al. |
| 2018/0192680 A1 * | 7/2018 | Fraser ..................... A23L 27/10 |
| 2018/0203921 A1 | 7/2018 | Privault et al. |
| 2018/0293489 A1 | 10/2018 | Eyster |
| 2018/0357299 A1 | 12/2018 | Miranda et al. |
| 2019/0171707 A1 | 6/2019 | Rapaport |
| 2019/0200797 A1 | 7/2019 | Diao et al. |
| 2019/0228855 A1 | 7/2019 | Leifer |
| 2019/0228856 A1 | 7/2019 | Leifer |
| 2019/0295440 A1 | 9/2019 | Hadad |
| 2020/0268032 A1 | 8/2020 | Okuyama |
| 2020/0309746 A1 | 10/2020 | Sakai |
| 2020/0365053 A1 | 11/2020 | Pichara et al. |
| 2021/0027379 A1 | 1/2021 | Zhu et al. |
| 2021/0117665 A1 | 4/2021 | Simantov et al. |

FOREIGN PATENT DOCUMENTS

| | | |
|---|---|---|
| WO | 2004083451 A1 | 9/2004 |
| WO | 2013052824 A1 | 4/2013 |
| WO | 2016010097 A1 | 1/2016 |
| WO | 2017070605 A1 | 4/2017 |
| WO | 2020237214 | 11/2020 |
| WO | 2021026083 A1 | 2/2021 |
| WO | 2021071756 A1 | 4/2021 |
| WO | 2022010503 A1 | 1/2022 |
| WO | 2022010544 A1 | 1/2022 |
| WO | 2022035464 A1 | 2/2022 |
| WO | 2022098381 A1 | 5/2022 |
| WO | 2022/235326 A1 | 11/2022 |
| WO | 2022/240439 A1 | 11/2022 |
| WO | 2022/265698 A | 12/2022 |
| WO | 2023080922 A1 | 5/2023 |
| WO | 2023080923 A1 | 5/2023 |

OTHER PUBLICATIONS

Mexico Patent Office, "The Granting Proceeds", in application No. MX/a/2020/006079, dated Aug. 24, 2022, 5 pages.
UK Patent Office, "Office Action", in application No. GB2118119.3, dated Aug. 16, 2022, 4 pages.
Fromm et al., "A Vector Space model for Neural Network Functions: Inspirations from Similarities between the Theory of Connectivity and the Logarithmic Time Course of Word Production", Frontiers in Systems Neuroscience, Aug. 28, 2020, 10 pages.
UK Patent Office, "Intention to Grant", in application No. GB2118119.3, dated Dec. 20, 2022, 2 pages.
International Searching Authority, "International Preliminary Report" in application No. PCT/US2020/034385, dated Dec. 2, 2021, 5 pages.
Canada Patent Office, "Commissioner's Notice—Application Found Allowable", in application No. 3,083,036, dated Feb. 24, 2022, 1 page.
UK Patent Office, "Office Action", in application No. GB2118119.3, dated Feb. 8, 2022, 8 pages.
The International Searching Authority, "Search Report" in application No. PCT/US2020/043330, dated Sep. 18, 2020, 16 pages.
The International Searching Authority, "Search Report" in application No. PCT/US2020/034385, dated Jul. 20, 2020, 7 pages.
Rudinger et al., "Skip-Prop: Representing Sentences with One Vector Pre Proposition", 12th International Conference on Computational Semantics, dated 2017, 7 pages.
Kramanolakis et al., "Item Recommendation with Variational Autoencoders and Heterogeneous Priors", DLRS, dated Oct. 18, , 5 pages.
Hui Zou et al., "Regularization and Variable Selection Via the Elastic Net", Department of Statistics, Stanford University, dated Dec. 5, 2003, 29 pages.
Current Claims in Canada application No. 3,083,036, dated Jun. 9, 2020, 5 pages.
Canada Patent Office, "Office Action", in application No. 3,083,036, dated Jul. 7, 2021, 5 pages.
Eating Bird Food, "Vegan "Chicken" Salad", https://www.eatingbirdsfood.com/simple-vegan-mock-chicken-salad/, Apr. 5, 2017, download Mar. 11, 2021, 2 pages.
Current Claims in application No. PCT/US2020/043330, dated Sep. 2020, 5 pages.
Bowman et al., "Generating Sentences from a Continuous Space", dated May 2016, 12 pages.
Current Claims in application No. PCT/US2020/034385, dated Jul. 2020, 5 pages.
Statement Regarding Pre-Filing Activities, dated Dec. 10, 2020, 2 pages.

(56) References Cited

OTHER PUBLICATIONS

Patel, U.S. Appl. No. 16/924,006, filed Jul. 8, 2020, Notice of Allowance.
Navon U.S. Appl. No. 16/989,413, filed Aug. 10, 2020, Notice of Allowance.
UK Patent Office, "Notification of Grant", in application No. GB2118119.3, dated Jan. 31, 2023, 2 pages.
Mexico Patent Office, "Office Action", in application No. MX/a/2020/006079, dated Jun. 1, 2022, 6 pages.
UK Patent Office, "Office Action", in application No. GB2118119.3, dated May 13, 2022, 5 pages.
springwise.com, "Artificial Intelligence Uses Algorithms to Make Nutritious Vegan Meat," https://springwise.com/artificial-intelligence-algorithms-vegan-meat/, last viewed May 5, 2023, 2 pages.
Malav et al. "Meat analogue: A Review, Critical Reviews in Food Science and Nutrition," DOI: 10.1080/10408398.2012.689381, 2013, 16 pages.
bbc.com, " Could AI help to create a meat-free world?", https://www.bbc.com/future/article/20171214-could-ai-help-create-a-meat-free-world, last viewed May 5, 2023, 7 pages.
Indian Patent Office, "Examination Report", in application No. 202014037032, dated Mar. 14, 2023, 7 pages.
Paul, Rahl, "Classifying Cooking Object's State using a Tuned VGG Convolutional Neural Netwrok," May 2018, 5 pages.
Rong, Xin. word2vec Parameter Learning Explained. arXiv:1411.2738v4 [cs.CL] Jun. 5, 2016. (Year: 2016).
Salvador, Amaia, et al. "Learning cross-modal embeddings for cooking recipes and food images." Proceedings of the IEEE conference on computer vision and pattern recognition. 2017. (Year: 2017).
David Xu, "Machine Learning for Flavor Development," Bachelor's Thesis, Harvard College, School of Engineering and Applied Sciences, Apr. 5, 2019, 69 pages.
Hattab et al., Application of an Inverse Neural Network Model for the Identification of Optimal Amendment to Reduce Copper Toxicity in Phytoremediated Contaminated Soils, Journal of Geochemical Exploration, Elsevier, 2014, 136, pp. 14-23, 2014. (Year: 2014).
Kieaibi E., Determination of Protein Secondary Structure from Infrared Spectra Using Partial Least-Squares Regression, 9 pages, 2016 (Year: 2016).
Yang et al., "Obtaining information about protein secondary structures in aqueous solution using Fourier transform IR spectroscopy", Published online Feb. 5, 2015, nature protocols, 16 pages.
XGBoost, "Python Package Introduction", https://xgboost.readthedocs.io/en/latest/python/python_intro.html, last viewed on Nov. 5, 2020, 5 pages.
Github.com, "CMBI/DSSP", https://github.com/cmbi/dssp, last viewed on Nov. 5, 2020. 4 pages.
Wilcox et al., "Determination of Protein Secondary Structure from Infrared Spectra Using Partial Least-Squares Regression", dated 2016 American Chemical Society, 9 pages.
Sigma-Aldrich, "IR Spectrum Table and Chart", https://www.sigmaaldrich.com/technical-documents/articles/biology/ir-spectrum-table.html, last viewed on Nov. 5, 2020, 6 pages.
Scipy.org, "scipy.signal.savgol_filter", https://docs.scipy.org/doc/scipy/reference/generated/scipy.signal.savgol_filter.html, last viewed on Nov. 5, 2020, 3 pages.
SciPy.org, "scipy.integrate.simps", https://docs.scipy.org/doc/scipy/reference/generated/scipy.integrate.simps.html, last viewed on Nov. 5, 2020, 2 pages.
Scikitlearn.org, "sklearn.neighbors.KNeighborsRegressor", https://scikit-learn.org/stable/modules/generated/sklearn.neighbors.KNeighborsRegressor.html, last viewed on Nov. 5, 2020, 5 pages.
Scikitlearn.org, "sklearn.model_selection.GridSearchCV", https://scikit-learn.org/stable/modules/generated/sklearn.model_selection.GridSearchCV.html, last viewed on Nov. 5, 2020, 7 pages.
Scikitlearn.org, "sklearn.linear_model.lasso", https://scikit-learn.org/stable/modules/generated/sklearn.linear_model.Lasso.html, last viewed on Nov. 5, 2020, 6 pages.
Scikitlearn.org, "sklearn.cross_decomposition.PLSRegression", https://scikit-learn.org/stable/modules/generated/sklearn.cross_decomposition.PLSRegression.html , last viewed on Nov. 5, 2020, 5 pages.
Scikitlearn.org, "3.2.4.1.3. sklearn.linear_model.LassoCV", https://scikit-learn.org/stable/modules/generated/sklearn.linear_model.LassoCV.html, last viewed on Nov. 5, 2020, 6 pages.
ProDry, "DSSP Tools", http://prody.csb.pitt.edu/manual/reference/proteins/dssp.html, last viewed on Nov. 5, 2020, 2 pages.
Cao et al.,"Optimization of Formulations Using Robotic Experiments Driven by Machine Learning DoE", Cell Reports Physical Science, Jan. 20, 2021, 17 pages.
International Searching Authority, "Search Report" in application No. PCT/US2020/034385, dated Jul. 20, 2020, 6 pages.
United States Patent Office, "Office Action", in U.S. Appl. No. 16/416,095, dated Jul. 29, 2019, 15 pages.
United States Patent Office, "Office Action", in U.S. Appl. No. 16/416,095, dated Dec. 16, 2019, 21 pages.
United States Patent Office, "Office Action", in U.S. Appl. No. 16/416,095, dated Nov. 4, 2020, 14 pages.
United States Patent Office, "Office Action", in U.S. Appl. No. 16/416,095, dated Mar. 16, 2021, 13 pages.
United States Patent Office, "Notice of Allowance", in U.S. Appl. No. 16/416,095, dated Jul. 21, 2021, 7 pages.
Yuan et al., "An Inductive Content-Augmented Network Embedding Model for Edge Artificial Intelligence", IEEE Transaction on Industrial Informatics, vol. 15 No. 7, Jul. 2019, pp. 4295-4305.
Hodgkin, "The Castlemaine Project: Development of an AI-based Drug Design Support System", Molecular Modelling and Drug Design, 1994, pp. 137-169.
Peiretti et al., "Artificial Intelligence: The Future for Organic Chemistry?", ACS Omega, 2018, 3 (10), pp. 13263-13266.
De Clercq et al., "Data-Driven Recipe Completion Using Machine Learning Methods, " Trends in Food Science & Technology 49 (2016), Dec. 2015, p. 1-13.
Pinel et al., Chapter 16: A Culinary Computational Creativity System, Computational Creativity Research: Towards Creative Machines, Jan. 2014, pp. 327-346.
Cromwell et al., "Computational Creativity in the Culinary Arts", Proceedings of the Twenty-Eighth International Florida Artificial Intelligence Research Society Conference, dated 2015, 5 pages.
Silva et al, "An expert system for automated flavour matching—Prioritizer", DOI: 10.1002/ffj.3386, 2017, 8 pages.
Severcan et al., "Estimation of protein secondary structure from FTIR spectra using neural networks", Journal of Molecular Structure 565-566 (2001) 383-397, 5 pages.
Hering et al., "An alternative method for rapid quantification of protein secondary structure from FTIR spectra using neural networks", Spectroscopy 16 (2002) 53-69, 18 pages.
Akkas et al., "Effects of lipoic acid supplementation on rat brain tissue: An FTIR spectroscopic and neural network study", Food Chemistry 105 (2007) 1281-1288, DOI:10.1016/j.foodchem.2007/03.015, 8 pages.
Indian Patent Office, "Search Report and Technical Examination Report", in application No. BR102020011594-4, dated Apr. 28, 2023, 12 pages.
Park et al., "FlavorGraph: a large-scale food-chemical grpah for generating food representations and recommending food pairings", Scientific Reports: nature Research, vol. 11, Jan. 13, 2021, 13 pages.

\* cited by examiner

102

| FIRST SOURCE INGREDIENT | 102a |
|---|---|
| FEATURE1 | 102a1 |
| FEATURE2 | 102a2 |
| FEATURE3 | 102a3 |
| . . . | |

| SECOND SOURCE INGREDIENT | 102b |
|---|---|
| FEATURE1 | 102b1 |
| FEATURE2 | 102b2 |
| FEATURE3 | 102b3 |
| . . . | |

| THIRD SOURCE INGREDIENT | 102c |
|---|---|
| . . . | |

. . .

| PTH SOURCE INGREDIENT | 102p |
|---|---|
| FEATURE1 | 102p1 |
| FEATURE2 | 102p2 |
| FEATURE3 | 102p3 |
| . . . | |

| | |
|---|---|
| FIRST TARGET INGREDIENT | <u>104a</u> |
| FEATURE 1 | <u>104a1</u> |
| FEATURE 2 | <u>104a2</u> |
| FEATURE 3 | <u>104a3</u> |
| . . . | |
| SECOND TARGET INGREDIENT | <u>104b</u> |
| FEATURE 1 | <u>104b1</u> |
| FEATURE 2 | <u>104b2</u> |
| FEATURE 3 | <u>104b3</u> |
| . . . | |
| THIRD TARGET INGREDIENT | <u>104c</u> |
| . . . | |
| . . . | |
| TTH TARGET INGREDIENT | <u>104t</u> |
| FEATURE 1 | <u>104t1</u> |
| FEATURE 2 | <u>104t2</u> |
| FEATURE 3 | <u>104t3</u> |
| . . . | |

| First Recipe | 402a |
|---|---|

| Name | 404 |
|---|---|
| Ingredients | 406 |

| First Ingredient | 406a |
|---|---|
| Ingredient Name | 406a1 |
| Quantity | 406a2 |
| State | 406a3 |

| Second Ingredient | 406b |
|---|---|
| ⋮ | |

⋮

| Fth Ingredient | 406f |
|---|---|

| Directions | 408 |
|---|---|

| First Instruction | 408a |
|---|---|
| ⋮ | |
| Gth Instruction | 408g |

| Second Recipe | 402b |
|---|---|
| ⋮ | |

⋮

| Hth Recipe | 402h |
|---|---|
| ⋮ | |

| FIRST RECIPE FORMULA | 602a |
|---|---|

| INGREDIENTS | 604 |
|---|---|

| FIRST SOURCE INGREDIENT | 102a |
|---|---|
| NAME | 604a1 |
| QUANTITY | 604a2 |

⋮

| MTH SOURCE INGREDIENT | 102m |
|---|---|

| COOKING PROCESS | 606 |
|---|---|

| FIRST INSTRUCTION | 606a |
|---|---|
| FIRST STEP | 606a1 |
| ⋮ | |
| JTH STEP | 606aj |

⋮

| NTH INSTRUCTION | 606n |
|---|---|

| PHOTOS | 608 |
|---|---|

| HUMAN FEEDBACK | 610 |
|---|---|
| FLAVOR | 610a |
| COLOR | 610b |

⋮

| SECOND RECIPE FORMULA | 602b |
|---|---|

⋮

| WTH RECIPE FORMULA | 602w |
|---|---|

IDENTIFY A SET OF FEATURES ASSOCIATED WITH A GIVEN TARGET FOOD ITEM USING A TARGET INGREDIENTS DATABASE. THE TARGET INGREDIENTS DATABASE IS CONFIGURED TO STORE A RESPECTIVE SET OF FEATURES FOR EACH OF A PLURALITY OF TARGET FOOD ITEMS
902

IDENTIFY TWO OR MORE SOURCE INGREDIENTS USING A SOURCE INGREDIENTS DATABASE BASED ON MATCHING OF THE IDENTIFIED SET OF FEATURES ASSOCIATED WITH THE GIVEN TARGET FOOD ITEM. THE SOURCE INGREDIENTS DATABASE IS CONFIGURED TO STORE A RESPECTIVE SET OF FEATURES FOR EACH OF A PLURALITY OF SOURCE INGREDIENTS
904

DETERMINE A FORMULA TO COMBINE THE TWO OR MORE SOURCE INGREDIENTS IN SPECIFIC PROPORTIONS TO MIMIC THE GIVEN TARGET FOOD ITEM
906

GENERATE THE RECIPE INCLUDING A COOKING PROCESS FOR THE FORMULA BASED ON A SET OF EXISTING RECIPES
908

```
┌─────────────────────────────────────────────────────────────────┐
│ PREPARE A TARGET INGREDIENTS DATABASE AND A SOURCE INGREDIENTS  │
│ DATABASE, EACH OF THE TARGET INGREDIENTS DATABASE AND THE SOURCE│
│ INGREDIENTS DATABASE DESCRIBED USING THE SAME TYPES OF FEATURES │
│ INCLUDING PHYSIOCHEMICAL, NUTRITIONAL AND MOLECULAR DESCRIPTORS │
│                              1002                               │
└─────────────────────────────────────────────────────────────────┘
                                 │
                                 ▼
┌─────────────────────────────────────────────────────────────────┐
│ CREATE A SCREENING OF A GIVEN TARGET FOOD ITEM AND A SET OF     │
│ SOURCE INGREDIENTS. THE SCREENING REPRESENTS EACH SOURCE        │
│ INGREDIENT IN A D-DIMENSIONAL SPACE BASED ON RESPECTIVE FEATURES│
│ RELATED TO PHYSIOCHEMICAL, NUTRITIONAL AND MOLECULAR DESCRIPTORS│
│                              1004                               │
└─────────────────────────────────────────────────────────────────┘
                                 │
                                 ▼
┌─────────────────────────────────────────────────────────────────┐
│ USE A FEATURE COMPRESSION METHOD TO DETERMINE A MORE COMPACT    │
│           REPRESENTATION OF THE FEATURE SPACE                   │
│                              1006                               │
└─────────────────────────────────────────────────────────────────┘
                                 │
                                 ▼
┌─────────────────────────────────────────────────────────────────┐
│ TRAIN A PREDICTION MODEL USING THE SET OF FEATURES OF THE SOURCE│
│ INGREDIENTS TO MATCH THOSE OF THE TARGET FOOD ITEM BASED ON A   │
│                  FEATURE SELECTION PROCESS                      │
│                              1008                               │
└─────────────────────────────────────────────────────────────────┘
                                 │
                                 ▼
┌─────────────────────────────────────────────────────────────────┐
│ SELECT MOST RELEVANT SOURCE INGREDIENTS USING THE PREDICTION    │
│ MODEL TO BE INCLUDED IN A FORMULA FOR A RECIPE TO MIMIC THE     │
│                       TARGET FOOD ITEM                          │
│                              1010                               │
└─────────────────────────────────────────────────────────────────┘
                                 │
                                 ▼
┌─────────────────────────────────────────────────────────────────┐
│ DETERMINE THE FORMULA USING AN OPTIMIZATION PROCESS TO DETERMINE│
│ A RESPECTIVE PROPORTION OF EACH OF THE MOST RELEVANT SOURCE     │
│                   INGREDIENTS IN THE FORMULA                    │
│                              1012                               │
└─────────────────────────────────────────────────────────────────┘
```

```
OBTAIN A SET OF EXISTING RECIPES FOR TRAINING A DEEP RECURRENT
NEURAL NETWORK (RNN). EACH EXISTING RECIPE CAN INCLUDE A LIST OF
             INGREDIENTS AND A SET OF INSTRUCTIONS
                            1102
```

```
PROCESS THE SET OF EXISTING RECIPES TO MODIFY EACH EXISTING RECIPE
             TO INCLUDE ONLY ATOMIC DIRECTIONS
                            1104
```

```
TRAIN THE DEEP RNN USING A FORMULA AND THE SET OF EXISTING RECIPES.
   THE RNN MAY PROVIDE A COOKING PROCESS COMPRISING A LIST OF
 ACTIONS AND RESPECTIVE INGREDIENTS USED TO GENERATE ONE OR MORE
              RECIPES TO MIMIC A TARGET FOOD ITEM
                            1106
```

```
GENERATE THE ONE OR MORE RECIPES USING THE TRAINED RNN FOR EACH
   TARGET FOOD ITEM. EACH RECIPE MAY INCLUDE A RESPECTIVE SCORE
 INDICATING A DIFFERENCE BETWEEN THE FORMULA AND THE TARGET FOOD
                            ITEM
                            1108
```

```
  SELECT A RECIPE BASED ON THE SCORE. THE SELECTED RECIPE CAN BE
 COOKED OR MODIFIED BY A CHEF. LATER, A SENSORIAL PANEL CAN TASTE
  THE FOOD PRODUCT AND GIVE FEEDBACK ON SENSORIAL DESCRIPTORS
                            1110
```

FIG. 11

SYSTEMS AND METHODS TO MIMIC TARGET FOOD ITEMS USING ARTIFICIAL INTELLIGENCE

BENEFIT CLAIM

This application is a continuation of U.S. non-provisional application Ser. No. 16/416,095, filed May 17, 2019, entire contents of which are hereby incorporated herein by reference for all purposes as if fully set forth herein. The applicant(s) hereby rescind any disclaimer of claim scope in the parent application(s) or the prosecution history thereof and advise the USPTO that the claims in this application may be broader than any claim in the parent application(s).

TECHNICAL FIELD

The disclosure generally relates to food science and artificial intelligence, in particular, use of machine learning to mimic target food items.

BRIEF DESCRIPTION OF THE FIGURES

FIG. 2 illustrates a source ingredients database configured to store a respective set of features for each of a plurality of source ingredients in certain embodiments;

FIG. 3 illustrates a target ingredients database configured to store a respective set of features for each of a plurality of target ingredients in certain embodiments;

FIG. 4 illustrates an example set of existing recipes that may be stored in an existing recipes database;

FIG. 5 illustrates processing steps for a recipe to include atomic directions according to certain embodiments;

FIG. 6 illustrates an example set of recipes that may be stored in a chef's database;

FIG. 9 illustrates a computer-implemented method to generate a recipe to mimic a given target food item according to certain embodiments;

FIG. 10 illustrates a computer-implemented method to determine a formula for a recipe to mimic a target food item; and FIG. 11 computer-implemented method to determine a recipe comprising a cooking process for the formula.

DETAILED DESCRIPTION

Figure 1:
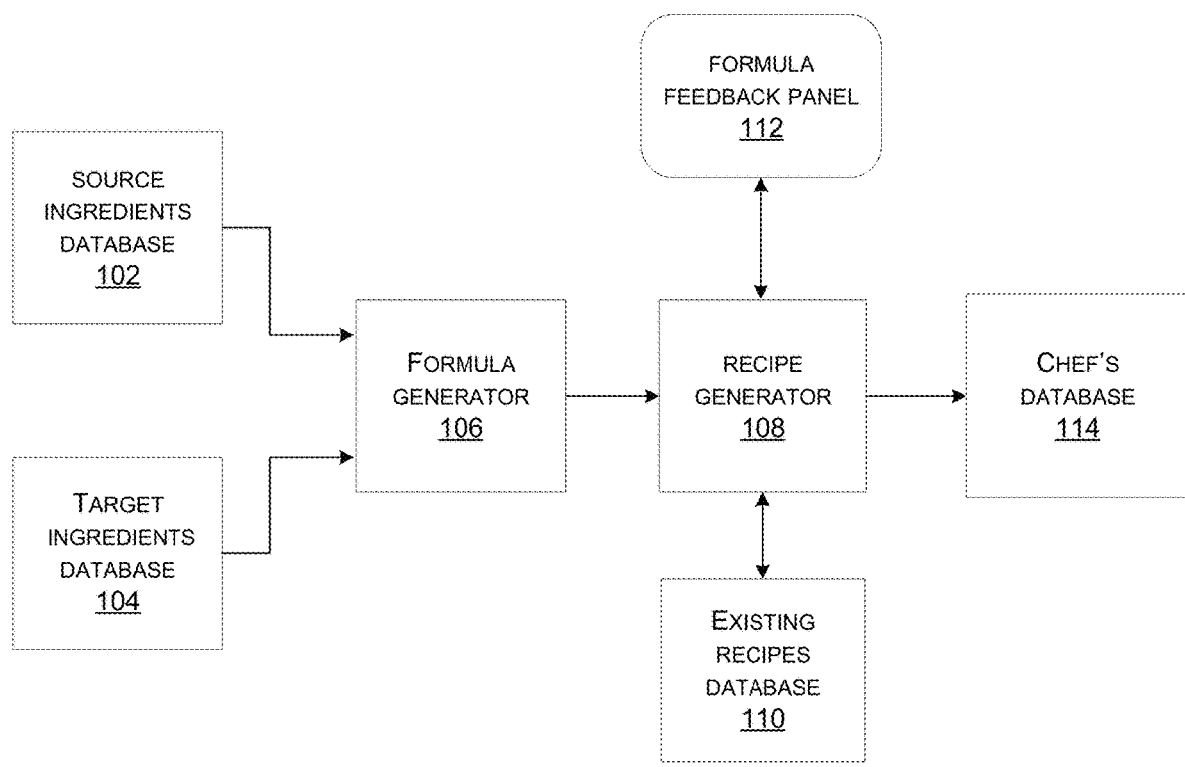
FIG. 1 illustrates a high-level diagram of a system that can utilize machine learning algorithms to generate a recipe using source ingredients to mimic a given target food item according to certain embodiments.

The following description of the embodiments is not intended to limit the invention to these embodiments, but rather to enable any person skilled in the art to make and use.

Today, many negative consequences of use of animals in the food industry are known, such as deforestation, pollution, human health conditions, and allergies among others. An animal-based food item can be a food product that includes any animal-based ingredient, such as cow milk and all dairy products, egg-based emulsions such as mayonnaise, meat-based foods such as beef hamburgers, sausages, etc. A number of products are available in the market that can provide substitutes for animal-based food, e.g., chicken, meat patties, milk, etc. The disclosed embodiments can utilize data science, food science and/or machine learning algorithms to find a combination of source ingredients that can taste, look and/or feel like a given target food item. The source ingredients and/or the target food item can be plant-based, animal-based or synthetic. Certain embodiments can provide recipes using plant-based ingredients that can mimic animal-based foods from the sensory (e.g., flavor and/or texture) and/or visual perspectives. In some examples, a combination of plant-based ingredients can be cooked using a certain recipe to taste, look and/or feel like cow milk.

In certain embodiments, the machine learning algorithms may include creating a screening of a given target food item and a plurality of source ingredients, e.g., a set of N source ingredients. In some examples, the given target food item can be animal-based and the source ingredients may include plant-based ingredients. In some examples, target food items can have any suitable basis (e.g., animal-based, plant-based, and/or synthetic, etc.) and the source ingredients can include any suitable combination of animal-based ingredients, plant-based ingredients, synthetic ingredients, and/or any suitable type of ingredients. The screening can represent each source ingredient in a D-dimensional space that includes features related to physicochemical, nutritional and/or molecular descriptors (e.g., where different source ingredients can have different feature values for the physicochemical, nutritional, and/or molecular descriptor features, etc.). Several prediction algorithms can be trained to match from the hypothesis space of the N source ingredients (used as data features) to the given target food item using a feature selection process. The prediction models can use one or more supervised machine learning approaches, e.g., gradient boosting trees and Lasso (least absolute shrinkage and selection operator) regression, to make predictions.

In certain embodiments, the prediction algorithms may use feature compression techniques such as kernel principal component analysis and/or auto-encoding for training the prediction model. In some other embodiments, the prediction model may be trained without any feature compression techniques. Once the prediction model is trained, the most important features used for the prediction may be selected as the potential candidates to mimic the target food item. After the potential candidates are selected, an optimization process can be executed to find a formula comprising specific proportions of the source ingredients to mimic the target food item.

Having estimated the combination of source ingredients to be used in the formula and their proportions, a cooking process may be discovered that can be applied to the selected source ingredients. The cooking process may also include actions to be taken and a sequence for performing the actions. For example, the actions may include grinding, mixing, boiling, frying, etc. In certain embodiments, one or more recurrent neural network (RNN) model(s) (and/or other suitable artificial intelligence models) may be trained with already existing recipes. Additionally, or alternatively, any suitable artificial intelligence approaches (e.g., described herein, etc.) can be applied (e.g., training of models, etc.) based on (e.g., trained with) any suitable recipes. The recipes may be obtained from the web and/or other sources (e.g., outputs of models described herein), and can be modified to include extensive manually processed tags that may contain necessary supervision to differentiate between an ingredient and a process. The modified recipes including the tags can be used as a main data source to train the RNN model(s) (and/or other artificial intelligence suitable models). The RNN model(s) (and/or other suitable artificial intelligence models) can be trained with the ingredients and various sequences for using these ingredients in the respective cooking processes. Given a set of ingredients based on the formula provided by the prediction model, the RNN model(s) (and/or other suitable artificial intelligence models) can be capable of sorting the given ingredients and predicting each of the ingredient processes(s) (and/or other suitable models). In certain embodiments, in the end (and/or at any suitable time), a full sequence of the cooking process representing a recipe formula to mimic the given target food item can be produced.

FIG. 1 illustrates a high-level diagram of a system 100 that can utilize machine learning algorithms to generate a recipe using source ingredients to mimic a given target food item in flavor, color, feel and/or functionality. The source ingredients can include plant-based ingredients, animal-based ingredients, water-based ingredients, synthetic ingredients, or a combination thereof. The target food item can also include plant-based ingredients, animal-based ingredients, water-based ingredients, synthetic ingredients, or a combination thereof. The system 100 may include a source ingredients database 102, a target ingredients database 104, a formula generator 106, a recipe generator 108, an existing recipes database 110, a formula feedback panel 112, and/or a chef's database 114.

Some non-limiting examples of the plant-based ingredients may include vegetables (e.g., onions, potatoes, garlic, spinach, carrots, celery, squash, etc.), fruit (e.g., apples, pears, grapes, etc.), herbs (e.g., oregano, cilantro, basil, etc.), spices (black peppers, turmeric, red chili peppers, cinnamon, etc.), oils (e.g., corn oil, olive oil), nuts (e.g., almonds, walnuts, pistachios, etc.), legumes (e.g., lentils, dried peas, soybeans, pulses, etc.), starch, proteins, fibers, carbohydrates, sugars, etc. Some non-limiting examples of the animal-based ingredients may include dairy products (e.g., milk, butter, cheese, yogurt, ice cream, etc.), egg-based products (e.g., mayonnaise, salad dressings, etc.), meat products (e.g., burger patties, sausages, hot dogs, bacon, etc.), and/or seafood (e.g., fish, crab, lobsters, etc.). Synthetic ingredients may include artificially produced food, e.g., artificial meats, artificial sweeteners, artificial milk, etc.

The source ingredients database 102 may be configured to store a respective set of features for each source ingredient in a plurality of source ingredients. The respective set of features for each source ingredient may include physiochemical, biochemical, nutritional, and/or molecular features. The physiochemical features may include data features associated with physical and/or chemical characteristics of a given source ingredient. The biochemical features may be associated with chemical processes occurring in the living organisms such as plants or animals. For example, Near-Infrared (NIR) spectroscopy techniques may be used to identify physical and/or chemical features of the ingredients. The nutritional features may include nutritional facts for the ingredient. The molecular features may include molecular formula or atomic arrangement of the ingredient. As an example, the set of features may include existing amino acids, vitamins, minerals (e.g., Magnesium, Manganese, Zinc, Sodium, Potassium, Selenium, Copper, Iron, Phosphorus, Calcium, Ash, etc.), carotenes, alcohol ethyl, alkaloids, fatty acids, carbohydrate, cholesterol, fibers, sugar, water, or protein. An example source ingredients database 102 is discussed with reference to FIG. 2.

As shown in FIG. 2, the source ingredients database 102 may store a plurality of source ingredients, e.g., a first source ingredient $102a$, a second source ingredient $102b$, a third source ingredient $102c$, and a Pth source ingredient $102p$. Each of the first source ingredient $102a$, the second source ingredient $102b$, the third source ingredient $102c$, and the Pth source ingredient $102p$ may include a respective set of features e.g., feature1, feature2, feature3, etc. The feature1 may be a first type of feature, the feature2 may be a second type of feature, the feature3 may be a third type of feature, and so on. As an example, a feature1 $102a1$, a feature1 $102b1$, . . . , and a feature1 $102p1$ may represent amino acids for the first source ingredient $102a$, the second source ingredient $102b$, and the Pth source ingredient $102p$ respectively. A feature2 $102a2$, a feature2 $102b2$, . . . , and a feature2 $102p2$ may represent vitamins for the first source ingredient $102a$, the second source ingredient $102b$, and the Pth source ingredient $102p$ respectively. A feature3 $102a3$, a feature3 $102b3$, . . . , and a feature3 $102p3$ may represent energy for the first source ingredient $102a$, the second source ingredient $102b$, and the Pth source ingredient $102p$ respectively. The source ingredients database 102 may be implemented using memory, e.g., random access memory (RAM), electrically erasable programmable read only memory (EEPROM), flash memory, hard disk drives, optical disc drives, solid state memory, or any type of memory suitable for database storage.

Referring back to FIG. 1, the target ingredients database 104 may additionally or alternatively be configured to store a respective set of features for each target ingredient in a plurality of target ingredients. The respective set of features stored in the target ingredients database 104 may include the same types of features as the source ingredients database 102, e.g., the physiochemical, biochemical, nutritional or molecular features, but the target ingredients database 104 can additionally or alternatively include different types of features as other databases (e.g., types of features included in the source ingredients database 102, etc.). In an example, the set of features associated with the given animal-based food item, the respective set of features for each of the plurality of food items (e.g., animal-based food items stored in a target ingredients database 104, etc.), and the respective set of features for each of the plurality of source ingredients (e.g., plant-based ingredients stored in a source ingredients database 102) can each be associated with a same set of feature types, such as where the same set of feature types comprises at least one of a nutritional descriptor feature type, a physiochemical descriptor feature type, and a molecular descriptor feature type. An example target ingredients database 104 is discussed with reference to FIG. 3.

As shown in FIG. 3, the target ingredients database 104 may store a first target ingredient $104a$, a second target ingredient $104b$, a third target ingredient $104c$, and a Tth target ingredient $104t$. Similar to the source ingredients database 102, each of the first target ingredient $104a$, the second target ingredient $104b$, the third target ingredient $104c$, and the Tth target ingredient $104t$ may include respective set of features feature1, feature2, feature3, and so on. As an example, a feature1 $104a1$, a feature1 $104b1$, . . . , and a feature1 $104t1$ may represent amino acids for the first target ingredient $104a$, the second target ingredient $104b$, and the Tth target ingredient $104t$ respectively. A feature2 $104a2$, a feature2 $104b2$, . . . , and a feature2 $104t2$ may represent vitamins for the first target ingredient $104a$, the second target ingredient $104b$, and the Tth target ingredient $104t$ respectively. A feature3 $104a3$, a feature3 $104b3$, . . . , and a feature3 $104t3$ may represent energy for the first target ingredient $104a$, the second target ingredient $104b$, and the Tth target ingredient $104t$ respectively. The target ingredients database 104 may be implemented using memory, e.g., RAM, EEPROM, flash memory, hard disk drives, optical disc drives, solid state memory, or any type of memory suitable for database storage.

Referring back to FIG. 1, the formula generator 106 may be configured to generate a formula for a given target food item using (e.g., based on, etc.) source ingredients from the source ingredients database 102. The formula may identify one or more source ingredients (e.g., two or more source ingredients, etc.) and/or their proportions. In some implementations, the formula generator 106 may create a screening of the target food item and a set of source ingredients. The set of source ingredients may include some or all of the first source ingredient 102a, the second source ingredient 102b, the third source ingredient 102c, and the Pth source ingredient 102p. The screening may represent each food item in a D-dimensional space comprising the physiochemical, nutritional or molecular features associated with the food item. For example, each food item can be represented in a vector space of multiple features associated with the physiochemical, nutritional or molecular properties.

The formula generator 106 may be configured to determine a formula comprising a set of source ingredients and/or their proportions that match a target in the feature space. In some examples, the formula generator 106 may identify a set of features associated with the given target food item using the target ingredients database 104. For example, the target may be the target food item (e.g., an animal-based brownie) and the source ingredients may be plant-based ingredients (e.g., lettuce, carrots, peanut butter). In some examples, one or more prediction models may be trained to match from the hypothesis space of the set of source ingredients (used as data features) to the given target food item using a feature selection process. Training of the prediction models may not use sensorial descriptors (e.g., flavor, color, texture or taste) as the data features for matching to the target food item, however the matching may indirectly correspond to mimicking the sensorial descriptor(s) of the target food item. The prediction model may be based on a gradient boosting tree for regression. The gradient boosting tree can be trained to fit a particular target by using the available physiochemical, nutritional or molecular features. Each target can be a new regression problem. A formula may be determined by presenting a feature selection problem to the trained prediction model where the features can be the source ingredients. The feature selection process may include selecting the most relevant features using the prediction model as the potential set of source ingredients to be included in the formula. The formula generator 106 may be further configured to execute an optimization process to find specific proportions for the selected source ingredients to generate the formula. In certain embodiments, Lasso optimization may be performed to balance the proportions of different ingredients in the set of source ingredients. For example, ingredients with almost negligible contribution (e.g., with a proportion less than 0.001%) may be deleted. In a variation, the formula generator 106 may be configured to determine a formula comprising a set of source ingredients, without determination of proportions of the source ingredients.

In some implementations, the prediction model(s) may use a feature compression technique such as kernel principal component analysis (KPCA) or auto-encoding; however, the prediction models can be trained with no feature compression steps. The KPCA or auto-encoding may provide techniques for non-linear feature extraction to reduce the dimensions of the features dataset. Note that any techniques for dimensionality reduction can be used without deviating from the scope of the disclosed technologies.

In certain embodiments, prediction model(s) (and/or other suitable models, such as recipe generator model(s), etc.), suitable components of embodiments of the system 100, and/or suitable portions of embodiments of methods described herein can include, apply, employ, perform, use, be based on, and/or otherwise be associated with artificial intelligence approaches (e.g., machine learning approaches, etc.) including any one or more of: supervised learning (e.g., using gradient boosting trees, using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminant analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and/or any suitable artificial intelligence approach.

Models described herein (e.g., formula prediction models, recipe generator models; etc.) can be run or updated: once; at a predetermined frequency; every time a certain process is performed; every time a trigger condition is satisfied and/or at any other suitable time and frequency. Models can be run or updated concurrently with one or more other models, serially, at varying frequencies, and/or at any other suitable time. Each model can be validated, verified, reinforced, calibrated, or otherwise updated based on newly received, up-to-date data; historical data or be updated based on any other suitable data.

The formula may be a combination of the selected source ingredients and/or their respective proportions meant to mimic the given target food item. For example, a formula $f_i$ may be defined as a set of $M_i$ pairs, each one comprising source ingredients and their respective proportions: $f_i = \{(p_1, I_1); (p_2, I_2); \ldots, (p_{Mi}, I_{Mi})\}$. Once the combination of source ingredients is obtained, the formula $f_i$ can be fed into the recipe generator 108 that can predict the order the source ingredients are meant to be used when cooking, and the actions (e.g., cut, boil, fry, stir, etc.) associated with the one or more source ingredients.

The recipe generator 108 may be configured to generate a recipe comprising a cooking process for the set of source ingredients in the formula to mimic the target food item. The cooking process may include a set of actions, tools, steps, and/or the respective proportions of the source ingredients based on the formula generated by the formula generator 106 (and/or by any suitable source). As an example, a recipe $r_i=\{f_i, Q_i\}$ may be defined as a 2D tuple comprising the formula $f_i$ and a sequence of processes $Q_i$. The sequence of processes $Q_i$ may be defined as $\{\{(a_1, t_1, h_1, \eta_1); (a_2, t_2, h_2, \eta_2); \ldots ; (a_{U_i}, t_{U_i}, h_{U_i}, \eta_{U_i})\}$, where each tuple $((a_m, t_m, h_m, \eta_m)$ $(m=[1 \ldots U_i])$ can be composed by an action $a_m$ (e.g., to boil), a tool $t_m$ (e.g., a pan), a step $h_m$ in the recipe sequence (e.g., a third step to be executed), and the set of source ingredients $\eta_m \{I_1, I_2, \ldots, I_{M_i}\}$ that are involved in the step $h_m$. Note that $U_i$ can be greater than or equal to $M_i$ because one ingredient may be used in more than one step associated with the $r_i$.

The recipe generator 108 may include a deep recurrent neural network that can be trained using existing recipes that have been previously generated. The existing recipes may be obtained from various websites or other sources, and can be processed to provide a structured dataset with a certain format. In some instances, the existing recipes may be collected by scraping various websites. The existing recipes may be stored in the existing recipes database 110. Each existing recipe may include raw text. As an example, each existing recipe may include a list of ingredients that may specify a name of each ingredient, quantity of each ingredient, and a state of each ingredient (e.g., four avocadoes, halved and pitted). Each existing recipe may also include directions to describe a list of instructions for cooking the ingredients. An example set of existing recipes is discussed with reference to FIG. 4. The set of existing recipes may be part of the existing recipes database 110.

FIG. 4 illustrates an example set of existing recipes 400 that may be stored in the existing recipes database 110. The set of existing recipes 400 may include a first recipe 402a, a second recipe 402b, . . . , and an Hth recipe 402h. Each of the recipes 402a, 402b, . . . , 402h may include a respective name, ingredients, and/or directions. For example, the first recipe 402a may include a name 404, an ingredients list 406, and directions 408. The ingredients list 406 may include a first ingredient 406a, a second ingredient 406b, . . . , and an Fth ingredient 406f. Each ingredient may include an ingredient name, a quantity and/or a state associated with it. For example, the first ingredient 406a may include an ingredient name 406a1, a quantity 406a2, and a state 406a3. Similarly, the directions 408 may include a set of instructions, e.g., a first instruction 408a, . . . , and a Gth instruction 408g. The set of existing recipes 400 may be processed by the recipe generator 108 to be used as a training set to train one or more RNN model(s) (and/or other suitable artificial intelligence models, etc.). For example, each recipe in the set of existing recipes 400 may be processed to have a specific format to prepare for training the RNN model. Processing of an example recipe is discussed with reference to FIG. 5.

Figure 5:
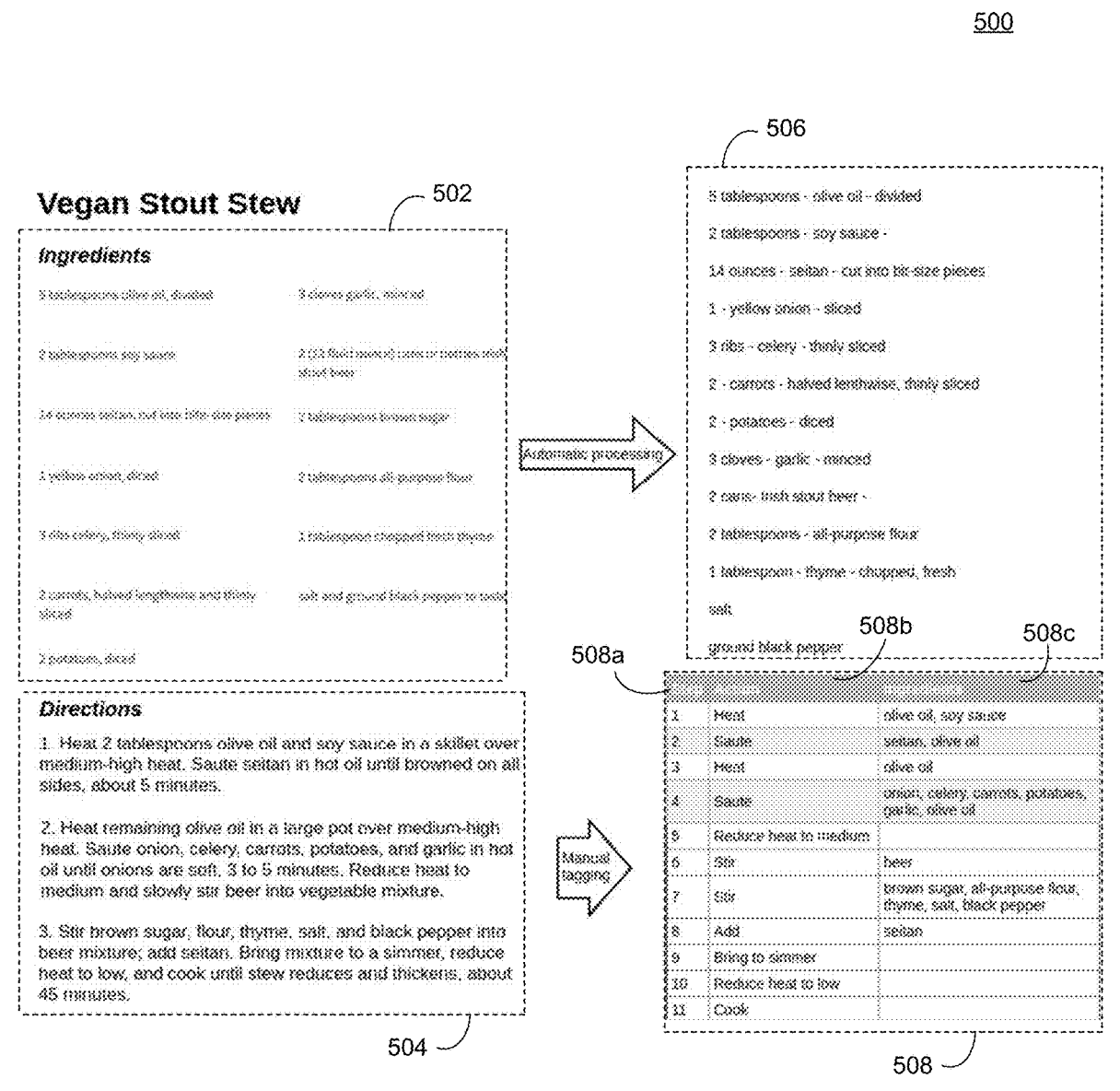

FIG. 5 illustrates processing of an existing recipe 500 for a vegan stout stew. The recipe 500 may belong to the set of existing recipes 400. For example, the recipe 500 may be the first recipe 402a, the second recipe 402b, . . . , or the Hth recipe 402h. The recipe 500 may have been obtained from an online website or another source. The recipe 500 may include an ingredients list 502 and/or directions 504. The recipe 500 may be processed by the recipe generator 108 to include a specific format to prepare for training one or more RNN model(s) (and/or other suitable artificial intelligence models, etc.). In some implementations, the processing may include a combination of automatic or manual processing. For example, the raw text of the ingredients list 502 may be automatically processed to identify ingredient names, quantities, and/or states as shown in a modified ingredients list 506. The modified ingredients list 506 may include ingredients from the ingredients list 502 represented as one or more words (e.g., olive oil, onion, salt, etc.). The quantity for each ingredient in the modified ingredients list 506 may or may not be specified and the measuring units may vary across the ingredients (e.g., 5 tablespoons olive oil, 1 yellow onion). Each ingredient can have zero or more states associated with it (e.g., divided, thinly sliced, minced, etc.).

The directions 504 may describe a set of instructions to cook the ingredients listed in the ingredients list 502. In certain embodiments, the directions 504 may be manually processed (and/or automatically processed) to include tags to differentiate between the words that correspond to an ingredient and the words that correspond to a cooking process. For example, the set of instructions in the directions 504 may be manually processed (and/or automatically processed) to include steps for cooking the ingredients as shown in a cooking process 508. In some implementations, each step can be a text paragraph including one or more atomic instructions with only one verb (or any suitable number of verbs and/or other types of words), and each atomic instruction can indicate an action to be performed on one or more ingredients. The cooking process 508 may include steps 508a for respective actions 508b to be performed on the respective ingredients 508c. For example, as shown in FIG. 5, a step 1 may indicate an action "heat" to be performed on the ingredients "olive oil" and "soy sauce." The ingredients 508c listed in the cooking process 508 may include all the ingredients from the ingredients list 502. In some examples, the cooking process 508 may also include tools (not shown) used in the process, e.g., a large pot, a skillet, a measuring spoon, etc.

Referring back to FIG. 1, the recipe generator 108 may use a set of existing recipes stored in the existing recipes database 110 as a training set to train one or more RNN model(s) (and/or other suitable artificial intelligence models, etc.). The RNN model(s) (and/or other suitable neural networks) can be a type of artificial neural network in which connections between nodes may form a directed graph along a temporal sequence. The RNN model(s) (and/or other suitable neural networks) can use its internal states to process sequence of inputs. The one or more RNN model(s) (and/or other suitable artificial intelligence models, etc.) may be trained to receive a formula $f_i$ generated by the formula generator 106 and to provide a list of actions and/or the respective source ingredients used for the cooking process to mimic a given target food item. In certain embodiments, to begin the generation of a new recipe for the target food item using the formula $f_i$, the source ingredients specified in the formula $f_i$ can be encoded as a one hot vector. To start the process, the one hot vector can be fed to the RNN model (and/or other suitable models) with a first reserved label (e.g., START), and a first action and one or more ingredients may be obtained. To generate the next action and its associated ingredients, the previous action can be added to a list of actions previously generated. The new list of actions and the list of ingredients can now be used as inputs to the one or more RNN model(s) (and/or other suitable artificial intelligence models, etc.). The generation of the new recipe may finish when a second reserved label (e.g., END) is returned.

A plurality of such recipes may be obtained for each target food item. For example, for a given target food item T, a set of recipes R={$r_1, r_2, \ldots, r_R$} can be generated. A score $s(f_i)$ based on a difference between the formula $f_i$ and the target food item T can be assigned to each recipe $r_i$ (i=[1 . . . R]). In some examples, the score $s(f_i)$ for each recipe can be calculated as $s(f_i)=\Sigma_{j=1}^{d} \Sigma_{k=1}^{Mi} [p_k * I_{kj} - T_j]$, where the formula $f_i$ can be extracted from its respective recipe $r_i$ using any suitable function $G(r_i)$. Herein, $p_k$ is a proportion of the ingredients $I_k$ included in the formula $f_i$, $I_{kj}$ is the value of the variable j in the ingredient $I_k$, and $T_j$ is the value of the target food item in the feature j. However, a score $s(f_i)$ can be determined in any suitable manner based on any suitable variables.

In an example, a set of recipes (e.g., including any generated recipes, etc.) can be generated, where each recipe of the set of recipes can include a respective cooking process for a respective formula, and where a score can be determined for each recipe of the set of recipes based on matching to the given target food item (e.g., matching of the formula to the given target food item, such as degree of difference between the formula and the given target food item; etc.).

Based on the score $s(f_i)$ (and/or other suitable data), one or more recipes may be picked and/or cooked by one or more persons (and/or machinery such as one or more robots, smart cooking appliances, and/or by any suitable entities and/or components, etc.). For example, the set of recipes R generated by the recipe generator 108 may be provided to the formula feedback panel 112. The formula feedback panel 112 may include a person to cook the one or more recipes, and/or a group of people to taste the cooked food item. For example, a chef may cook many recipes for one target or can cook one recipe in many different ways. The chef may cook the recipe as is, or can vary proportions or ingredients (e.g., slightly; greatly; by a percentage amount; by an absolute amount; based on a chef's manual actions; based on recommendations and/or other outputs of one or more models; etc.) as specified by the recipe formula. A feedback on the cooked food item may be provided by the chef and/or by the group of people. For example, the feedback may include feedback on sensorial descriptors (e.g., color, flavor, taste, mouthfeel, etc.) as well as visual appearances. In some instances, the feedback provided by the formula feedback panel 112 may include a modified recipe formula. The modified recipe formula, its preparation, one or more pictures, the sensorial feedback, and/or any other relevant information can be saved into the chef's database 114. In some examples, the recipes generated by the recipe generator 108 may be in the format similar to the modified ingredients list 506 and/or the cooking process 508. In other example, the recipes may have been modified by the recipe generator 108 to include free text, similar to the ingredients 502 and the directions 504. Free text-based recipes can be generated manually, automatically (e.g., using any suitable types of models described herein, etc.), and/or through any suitable means. An example set of recipe formulas, which may be stored in the chef's database 114, is discussed with reference to FIG. 6.

FIG. 6 illustrates an example set of recipes 600 which may be stored in the chef's database 114. The set of recipes 600 may be generated using the system 100 in FIG. 1. The set of recipe formulas 600 may include a first recipe formula 602a, a second recipe formula 602b, . . . , and a Wth recipe formula 602w. The first recipe formula 602a may include a list of ingredients 604, a cooking process 606, photos 608, and human feedback 610. The list of ingredients 604 may include two or more source ingredients from the plurality of source ingredients 102a-102p as discussed with reference to FIG. 2. For example, the list of ingredients 604 may include the first source ingredient 102a. Each ingredient may include a respective name and/or quantity. For example, the first source ingredient 102a may include a name 604a1 and a quantity 604a2.

The cooking process 606 may include a set of instructions for cooking the ingredients 604. For example, the cooking process 606 may include a first instruction 606a, . . . , and an Nth instruction 606n. Each instruction may include multiple steps. For example, the first instruction 606a may include a first step 606a1, . . . , and a Jth step 606aj. In some examples, each instruction 606a-606n may be in the same format as each instruction in the directions 504.

The photos 608 may include pictures of the ingredients, the cooked food, or intermediate stages of the cooking process 606. The human feedback 610 may include a flavor 610a, a color 610b, and/or any other sensorial feedback. The flavor 610a may include a flavor of the cooked food and the color 610b may include a color of the cooked food. As an example, the human feedback 610 may be provided by the formula feedback panel 112.

In certain embodiments, the set of recipes 600 may include multiple versions of the same recipe to mimic a specific target food item. As an example, the first recipe formula 602a may correspond to an original recipe generated by the recipe generator 108 for a target food item, and the second recipe formula 602b may correspond to a modified recipe based on the formula feedback panel 112. Similarly, multiple versions of a recipe may be stored with different variations, and/or corresponding photos and/or human feedback.

Figure 7:
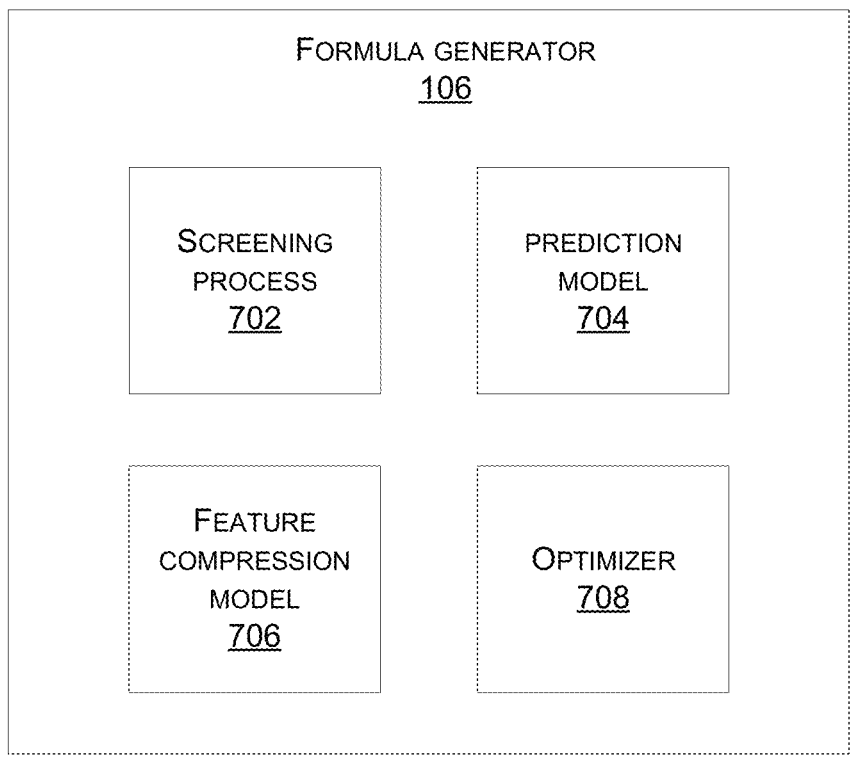
FIG. 7 illustrates a block diagram for a formula generator in certain embodiments.

FIG. 7 illustrates a block diagram 700 for the formula generator 106 of FIG. 1. In some implementations, the formula generator 106 may include a screening process 702, a prediction model 704, a feature compression model 706, and/or an optimizer 708. Note that components of the formula generator 106 may be implemented using software, hardware, firmware or a combination thereof. In some implementations, one or more components of the formula generator 106 may include a processor configured to execute instructions stored in a non-transitory computer readable medium.

The screening process 702 may be used to create a screening of the target food item and/or the source ingredients in a plurality of source ingredients. The screening may represent each food item in a D-dimensional space that may contain features related to physiochemical, nutritional and/or molecular descriptors (e.g., where different source ingredients can have different feature values for the physicochemical, nutritional, and/or molecular descriptor features, etc.). For example, each food item can be represented in a vector space of multiple features associated with the physiochemical, nutritional or molecular descriptors. As discussed with reference to FIG. 2 and FIG. 3, the features associated with the source ingredients may be stored in the source ingredients database 102 and/or the features associated with the target food item may be stored in the target ingredients database 104. The screening process 702 may be configured to identify a set of features associated with the given target food item using the target ingredients database 104 by creating a screening of the target food item and the plurality of source ingredients.

The prediction model 704 may be implemented using a machine learning technique for regression such as gradient boosting trees. The prediction model 704 may be trained to match from the hypothesis space of the plurality of source ingredients (used as data features) to a target. For example, the gradient boosting trees can be trained to fit a particular target by using the available physiochemical, nutritional or molecular features. A formula may be determined by presenting a feature selection problem to the trained prediction model where the features can be the source ingredients. The most relevant features selected using the prediction model 704 can be the potential set of source ingredients to be included in the formula. Training the prediction model 704 to match the set of features for each of the plurality of source ingredients to the identified set of features associated with the target food items may indirectly correspond to mimicking the sensorial descriptors (e.g., flavor, color, texture, or taste) of the target food item; however, the set of features used for the matching may not directly include the sensorial descriptors of the target food item. Additionally or alternatively, any suitable artificial intelligence approach (e.g., described herein, etc.) can be used for the prediction model 704.

In certain embodiments, the feature compression model 706 may be used to perform feature compression, e.g., kernel principal component analysis (KPCA) or auto-encoding. In some other embodiments, the prediction model 704 can be trained without any feature compression. For example, the feature compression may be performed to reduce the dimensions of the features dataset.

The optimizer 810 may be used to execute an optimization process to determine specific proportions of the selected source ingredients to generate the formula. In some examples, Lasso optimization may be performed to determine the proportions of different source ingredients in the set of source ingredients. Note that other techniques for finding the optimal proportions of the source ingredients in the formula are possible within the scope of the disclosed technologies.

Figure 8:
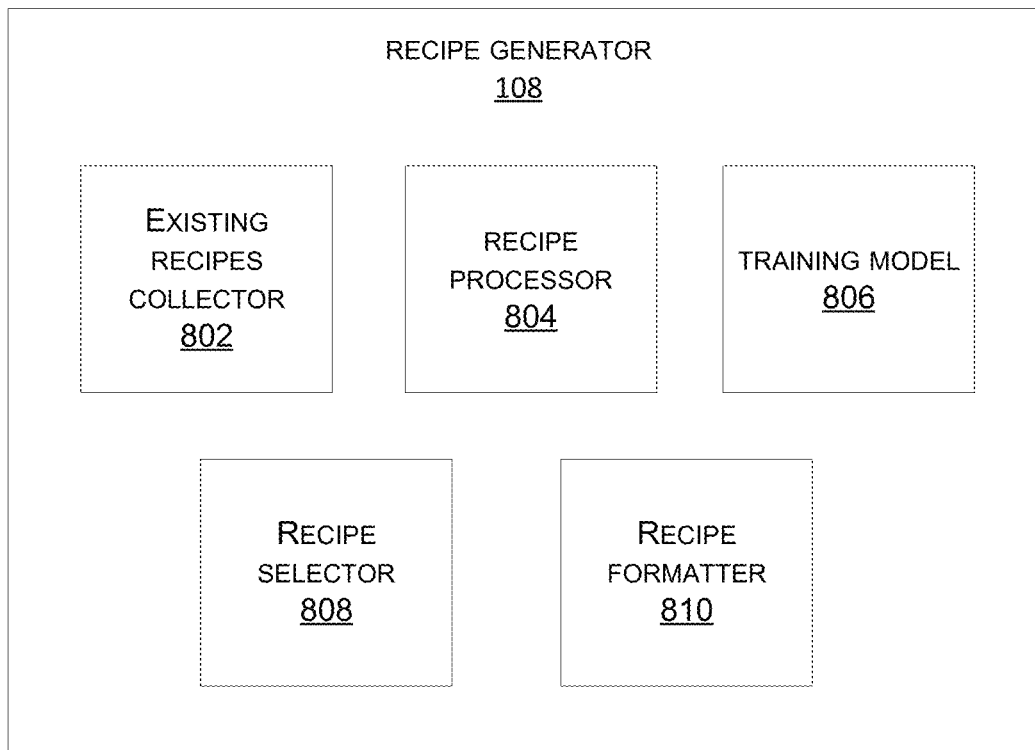
FIG. 8 illustrates a block diagram for a recipe generator in certain embodiments.

FIG. 8 illustrates a block diagram 800 for the recipe generator 108 of FIG. 1. In some implementations, the recipe generator 108 may include an existing recipes collector 802, a recipe processor 804, a training model 806, a recipe selector 808, and/or a recipe formatter 810. Note that components of the recipe generator 108 may be implemented using software, hardware, firmware or a combination thereof. In some implementations, one or more components of the recipe generator 108 may include a processor configured to execute instructions stored in a non-transitory computer readable medium.

The existing recipes collector 802 may be configured to obtain existing recipes from online websites, manual inputs, or other suitable sources. The existing recipes collector 802 may be configured to obtain existing recipes automatically (e.g., through APIs and/or other data requests for retrieving recipes, scraping, etc.), manually (e.g., through manual inputs, etc.), and/or through any suitable means. The existing recipes may be processed to include a specific format and/or can be used as training data to determine a cooking process for the set of source ingredients provided in the formula to mimic a target food item. The existing recipes may be stored in the existing recipes database 110 as discussed with reference to FIG. 4. The existing recipes may include recipes similar to the recipe 500 discussed with reference to FIG. 5.

The recipe processor 804 may be configured to perform automatic and/or manual processing of the existing recipes stored in the existing recipes database 110. The automatic and/or manual processing may be used to differentiate between the words corresponding to the ingredients and the words corresponding to a process by tagging the corresponding words. As discussed with reference to FIG. 5, the recipe 500 may be processed to provide the modified ingredients list 506 comprising the ingredients name, quantity and/or states, and/or the cooking process 508 comprising the atomic directions for the respective ingredients.

The training model 806 may implement one or more RNN model(s) (and/or other suitable artificial intelligence models, etc.) that can be used to determine a cooking process for the set of ingredients in the formula. The one or more RNN model(s) (and/or other suitable artificial intelligence models, etc.) can be trained over a sequence of ingredients and/or their respective processes from the existing recipes. The training model 806 may be capable of sorting a given set of source ingredients and predicting each of the source ingredient processes, ending up in a full sequence that may represent a full food recipe to mimic a given target food item. In certain embodiments, to begin the generation of a new recipe for the target food item using the formula $f_i$, the source ingredients specified in the formula $f_i$ can be encoded as a one hot vector. To start the process, the one hot vector can be fed to the training model 806, and a first action and/or one or more ingredients may be obtained. To generate the next action and its associated ingredients, the previous action can be added to a list of actions previously generated. This process can repeat until a full sequence of source ingredients representing a complete food recipe is obtained.

The recipe selector 808 may select one or more recipes provided by the training model 806. In some examples, the training model 806 may provide a plurality of recipes for each target food item. For example, for a given target food item, a set of recipes can be generated. In certain embodiments, the recipe selector 808 may select the one or more recipes based on a score $s(f_i)$. The score $s(f_i)$ may indicate how similar the formula is to the target food item in the feature space. As an example, a lower score (e.g., based on a smaller difference between a formula and features of a target food item, etc.) may indicate that the recipe is closer in the feature space to the target food item. As another example, a higher score (e.g., based on suitable calculations, etc.) can be used to indicate preferable recipes (e.g., recipes closer in the feature space to the target food item, etc.). The selected one or more recipes may be provided to the formula feedback panel 112 for the feedback. The one or more recipes may be cooked by a chef and the human feedback on any suitable combination of sensorial descriptors (e.g., color, flavor, taste, mouthfeel, etc.) and/or visual appearances may be collected. In some examples, the one or more recipes may be modified based on the feedback. In some instances, the feedback provided by the formula feedback panel 112 may include a modified recipe formula. The modified recipe formula, its preparation, one or more pictures, the sensorial feedback, and/or any other relevant information can be saved into the chef's database 114 as discussed with reference to FIG. 6.

The recipe formatter 810 may be configured to format the recipes in a certain format for storing in the chef's database 114. For example, each respective recipe formula may be stored with a certain format in the chef's database 114 as discussed with reference to FIG. 6. In some examples, the recipes generated by the recipe generator 108 may be in the format similar to the modified ingredients list 506 and/or the cooking process 508. In other example, the recipes may have been modified by the recipe generator 108 to include free text, similar to the ingredients 502 and/or the directions 504.

However, embodiments of a system 100 can be configured in any suitable manner.

FIG. 9 illustrates a computer-implemented method 900 to generate a recipe to mimic a given target food item. The method 900 may be executed by any suitable embodiments of the system 100 (e.g., of FIG. 1).

In step 902, a set of features associated with the given target food item may be identified using a target ingredients database. The target ingredients database may be configured to store a respective set of features for each of a plurality of target food items. For example, the set of features associated with the given target food item can be identified using the target ingredients database 104. The set of features associated with the target food item may include one or more of the feature1, feature2, feature3, etc. for the respective target ingredient. In some examples, the target ingredients database 104 may store a respective set of features for each of a plurality of animal-based food items (and/or any suitable type of food items, etc.). The respective set of features may include amino acids, vitamins, carbohydrates, fiber, color, smell, and/or texture, etc.

In step 904, two or more source ingredients may be identified using a source ingredients database based on matching of the identified set of features associated with the target food item. The source ingredients database may be configured to store the respective set of features for each of a plurality of source ingredients. As an example, the two or more source ingredients may be identified using the source ingredients database 102. In some examples, the source ingredients database 102 may store a respective set of features for each of a plurality of plant-based food items (and/or any suitable types of food items, etc.). The feature types of the respective set of features may be the same as the feature types of the set of features associated with the target food item, e.g., amino acids, vitamins, carbohydrates, fiber, color, smell, and/or texture, other feature types, etc. In certain embodiments, the formula generator 106 may identify the two or more source ingredients by training the prediction model 704 to match the respective set of features for each of the plurality of source ingredients to the identified set of features associated with the target food items.

In step 906, a formula can be generated to combine the two or more source ingredients from the plurality of source ingredients in specific proportions based on matching of the set of features associated with the given target food item. As discussed with reference to FIG. 1, the formula generator 106 may be used to generate the formula $f_i$ to combine the two or more source ingredients in specific proportions based on matching of the set of features associated with the given target food item T using a feature selection process. The formula generator 106 may use the optimizer 708 to execute an optimization process to determine the specific proportions for combining the two or more source ingredients in the formula.

In step 908, a recipe including a cooking process for the formula is generated based on a set of existing recipes. The set of existing recipes may be similar to the set of existing recipes 400. The set of existing recipes may be obtained from online resources and stored in the existing recipes database 110. The cooking process may be determined by the recipe generator 108 using the formula. The cooking process may include actions to be taken on the two or more source ingredients and/or a sequence for performing the actions. For example, the actions may include cutting, boiling, mixing, etc.

The recipe generator 108 may use the training model 806 to generate one or more recipes based on the training dataset and/or the formula. The training dataset may be prepared using the set of existing recipes collected by the existing recipes collector 802 and modified by the recipe processor 804 to support a specific format. The recipe selector 808 may select the recipe to mimic the given target food item from the one or more recipes generated by the recipe generator 108 based on a respective score $s(f_i)$ associated with each of the one or more recipes $r_i$. In some examples, the recipe may be provided to the formula feedback panel 112 for feedback. The recipe may be cooked by a person and a feedback on the taste and/or other sensorial descriptors may be provided by the chef and/or a group of people who tasted the cooked food item. Based on the feedback, the recipe may be modified and/or stored in the chef's database 114.

FIG. 10 illustrates a computer-implemented method 1000 for determining a formula for a recipe to mimic a target food item. The computer-implemented method 1000 may be executed using any suitable embodiments of the system 100 of FIG. 1 to determine a formula for a recipe to mimic the target food item using source ingredients. The target food item or the source ingredients may be plant-based, animal-based, or artificially generated (e.g., synthetic) food items.

In step 1002, a target ingredients database and/or a source ingredients database can be prepared. Each of the target ingredients database and the source ingredients database may be described using the same types of features, e.g., physiochemical, nutritional and molecular descriptors (and/or different types of features). As discussed with reference to FIGS. 1-3, the target ingredients database 104 and the source ingredients database 102 can include the same types of features, e.g., feature1, feature2, feature3, etc. (and/or different features).

In step 1004, a screening of a given target food item and a set of source ingredients can be created. The screening may represent each source ingredient in a D-dimensional space based on (e.g., that contains) their respective set of features including physiochemical, nutritional and/or molecular descriptors (e.g., where different source ingredients can have different values for the physicochemical, nutritional, and/or molecular descriptor features, etc.). As discussed with reference to FIG. 7, the formula generator 106 may use the screening process 702 to create a screening of the given target food item and the set of source ingredients.

In an optional step 1006, a feature compression method to determine a more compact representation of the feature space may be executed. As discussed with reference to FIG. 7, the formula generator 106 may use the feature compression model 706 to perform feature compression in order to reduce the dimensions of the features dataset, if desired. The feature compression model 706 may use kernel principal component analysis (KPCA), auto-encoding or another suitable method for feature compression.

In step 1008, a prediction model may be trained using the set of features of the source ingredients to match those of the target food item based on a feature selection process. As discussed with reference to FIG. 7, the formula generator 106 may use the prediction model 704 implemented using gradient boosting trees regression model. The prediction model 704 may be trained to match from the hypothesis space of the plurality of source ingredients (used as data features) to a target. For example, the gradient boosting trees can be trained to fit a particular target by using the available physiochemical, nutritional or molecular features.

Step 1010 can include selecting the most relevant source ingredients using the prediction model to be included in a formula for a recipe to mimic the target food item. The formula generator 106 may use the prediction model 704 to determine a formula $f_i$ by presenting a feature selection problem to the trained prediction model 704 where the features can be the source ingredients. The most relevant features selected using the prediction model 704 can be the potential set of source ingredients to be included in the formula.

Step 1012 can include determining the formula using an optimization process to determine a respective proportion of each of the most relevant source ingredients in the formula $f_i$. The formula generator 106 may use the optimizer 810 to execute an optimization process to determine specific proportions of the most relevant ingredients to generate the formula $f_i$.

FIG. 11 illustrates a computer-implemented method 1100 for determining a recipe comprising a cooking process for the formula generated by executing any suitable embodiments of the method 1000. The computer-implemented method 1100 may be executed using any suitable embodiments of the system 100 of FIG. 1.

In step 1102, a set of existing recipes may be obtained for training a deep RNN (and/or any suitable artificial intelligence model). Each existing recipe can include a list of ingredients and a set of instructions. As discussed with reference to FIG. 8, the existing recipes collector 802 may obtain a set of existing recipes from online resources. For example, the set of existing recipes may include the set of recipes 400.

In step 1104, the set of existing recipes may be processed to modify each existing recipe to include only atomic directions. As discussed with reference to FIG. 5 for the example recipe 500, the ingredients list 502 and/or the directions 504 may be modified using automatic and manual processing to include atomic directions for the respective ingredients as shown by the cooking process 508. For example, the atomic directions may include "heat", "sauté", "stir", "cook", etc. In some examples, the set of existing recipes may be stored in the existing recipes database 110.

In step 1106, the one or more RNN model(s) (and/or other suitable artificial intelligence models, etc.) may be trained using the formula and/or the set of existing recipes. The one or more RNN model(s) (and/or other suitable artificial intelligence models, etc.) may provide a cooking process comprising a list of actions and/or respective ingredients used to generate one or more recipes to mimic the target food item. As discussed with reference to FIG. 8, the training model 806 implementing the one or more RNN model(s) (and/or other suitable artificial intelligence models, etc.) may be trained using the formula $f_i$ generated by the formula generator 106 and the set of existing recipes modified by the recipe processor 804. The training model 806 may provide a cooking process similar to the cooking process 508 comprising a list of actions and respective ingredients used to generate one or more recipes to mimic the target food item.

In step 1108, one or more recipes may be generated using the trained one or more RNN model(s) (and/or other suitable artificial intelligence models, etc.) for each target food item. Each recipe may include a respective score indicating a difference between the formula $f_i$ and the target food item. As discussed with reference to FIG. 8, the training model 806 may be used to generate the one or more recipes. Each recipe may include a respective score $s(f_i)$. The score $s(f_i)$ may indicate how similar the formula is to the target food item in the feature space. As an example, a lower score may indicate that the recipe is closer in the feature space to the target food item.

In step 1110, a recipe may be selected from the one or more recipes based on the score. The selected recipe can be cooked or modified by a chef (and/or robot, smart cooking appliance, and/or any suitable entity). Later a sensorial panel can taste the cooked food product and can give feedback on sensorial descriptors. The selected one or more recipes may be provided to the formula feedback panel 112 for the feedback. As discussed with reference to FIG. 6, the one or more recipes may be cooked by a chef (and/or other suitable entity) and the human feedback on sensorial descriptors (e.g., color, flavor, taste, mouthfeel, etc.) as well as visual appearances may be collected. In some examples, the one or more recipes may be modified based on the feedback. In some instances, the feedback provided by the formula feedback panel 112 may include a modified recipe formula. The modified recipe formula, its preparation, one or more pictures, the sensorial feedback, and/or any other relevant information can be saved into the chef's database 114.

One or more instances and/or portions of embodiments of the methods and/or processes described herein can be performed asynchronously (e.g., sequentially), concurrently (e.g., in parallel; concurrently on different threads for parallel computing to improve system processing ability; etc.), in temporal relation to a trigger event (e.g., performance of a portion of an embodiment of a method descried herein), and/or in any other suitable order at any suitable time and frequency by and/or using one or more instances of embodiments of the system 100, components, and/or entities described herein.

As discussed with reference to FIGS. 1-11, the disclosed embodiments can utilize various machine learning algorithms and/or proprietary databases to generate recipes for given target food items using different types of source ingredients. Certain embodiments can provide flexibility in generating recipes for any given type of a target food item (e.g., plant-based, animal-based or synthetic) using any type of source ingredients (e.g., plant-based, animal-based or synthetic).

Portions of embodiments of methods and/or systems described herein are preferably performed by a first party but can additionally or alternatively be performed by one or more third parties, users, and/or any suitable entities Additionally or alternatively, data described herein can be associated with any suitable temporal indicators (e.g., seconds, minutes, hours, days, weeks, time periods, time points, timestamps, etc.) including one or more: temporal indicators indicating when the data was collected, determined (e.g., output by a model described herein), transmitted, received, and/or otherwise processed; temporal indicators providing context to content described by the data; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data can be associated with value types including any one or more of: scores (e.g., recipe scores, etc.), text values (e.g., indicating ingredients, actions, etc.), numerical values (e.g., indicating proportions for ingredients; indicating aspects of atomic directions, etc.), binary values, classifications, confidence levels, identifiers, values along a spectrum, and/or any other suitable types of values. Any suitable types of data described herein can be used as inputs (e.g., for different models described herein; for components of a system 100; etc.), generated as outputs (e.g., of models; of components of a system 100; etc.), and/or manipulated in any suitable manner for any suitable components.

Additionally or alternatively, suitable portions of embodiments of methods and/or systems described herein can include, apply, employ, perform, use, be based on, and/or otherwise be associated with one or more processing operations including any one or more of: extracting features, performing pattern recognition on data, fusing data from multiple sources, combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), normalization, updating, ranking, weighting, validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, interpolating, extrapolating, clustering, image processing techniques, other signal processing operations, other image processing operations, visualizing, and/or any other suitable processing operations.

Embodiments of the system 100 and/or portions of embodiments of the system 100 can entirely or partially be executed by, hosted on, communicate with, and/or otherwise include one or more: remote computing systems (e.g., one or more servers, at least one networked computing system, stateless, stateful; etc.), local computing systems, mobile phone devices, other mobile devices, personal computing devices, tablets, databases, application programming interfaces (APIs) (e.g., for accessing data described herein, etc.) and/or any suitable components. Communication by and/or between any components of the system 100 and/or other suitable components can include wireless communication (e.g., WiFi, Bluetooth, radiofrequency, Zigbee, Z-wave, etc.), wired communication, and/or any other suitable types of communication.

Components of embodiments of the system 100 can be physically and/or logically integrated in any manner (e.g., with any suitable distributions of functionality across the components, such as in relation to portions of embodiments of methods described.

Embodiments of the method 900, system 100, and/or any suitable systems and/or methods described herein and/or variants thereof can include every combination and permutation of the various system components and the various method processes, including any variants (e.g., embodiments, variations, examples, specific examples, figures, etc.), where portions of the method 900 and/or processes described herein can be performed asynchronously (e.g., sequentially), concurrently (e.g., in parallel), or in any other suitable order by and/or using one or more instances, elements, components of, and/or other aspects of the system 100 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

The system 100, method 900, and/or any suitable systems and/or methods described herein and/or variants thereof can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the system 100, method 900, and/or variants without departing from the scope defined in the following claims.

What is claimed is:

1. A computer-implemented method to generate a recipe using plant-based ingredients to mimic a given animal-based food item, the method comprising:
    receiving matching plant-based source ingredients from a plurality of plant-based source ingredients that match an animal-based target food item in a feature space of the plurality of plant-based source ingredients;
    applying a machine learning generator model to the at least the matching plant-based source ingredients to generate a recipe that uses the matching plant-based source ingredients to mimic the animal-based target food item, the recipe comprising a cooking process,
    wherein the machine learning generator model is trained using a training set, the training set comprising a set of processed existing recipes stored in an existing recipes database, each existing recipe in the set of processed existing recipes including a list of ingredients and a list of instructions for cooking the ingredients in the list of ingredients.

2. The computer-implemented method of claim 1, further comprising:
    retrieving, from a target database, a set of data features associated with the animal-based target food item, the set of data features for the animal-based target food item comprising at least one of:
        physiochemical data features of the animal-based target food item,
        nutritional data features of the animal-based target food item, or
        molecular data features of the animal-based target food item;
    retrieving, from a source ingredients database, a respective set of data features for each of the plurality of plant-based source ingredients, the respective set of data features for each of the plant-based source ingredients comprising at least one of:
        physiochemical data features of the plant-based source ingredient,
        nutritional data features of the plant-based source ingredient, or
        molecular data features of the plant-based source ingredient;
    creating a different training set from the respective set of data features for each of the plurality of plant-based source ingredients;
    training a machine learning prediction model by using the different training set to generate the feature space of the plurality of plant-based source ingredients.

3. The computer-implemented method of claim 2, further comprising:

executing a computer-implemented feature compression method on the respective set of data features for each of the plurality of plant-based source ingredients, to determine a compact representation of the respective set of data features for each of the plurality of plant-based source ingredients, wherein the different training set comprises the compact representation of the respective set of data features for each of the plurality of plant-based source ingredients.

4. The computer-implemented method of claim 2, wherein the set of data features associated with the animal-based target food item and the respective set of data features for each of the plurality of plant-based source ingredients are each associated with a same set of data feature types, and wherein the same set of data feature types comprises at least one of:
a nutritional descriptor feature type,
a physiochemical descriptor feature type, or
a molecular descriptor feature type.

5. The computer-implemented method of claim 2, wherein the machine learning prediction model is based on gradient boosting trees, and wherein the machine learning generation model is based on a recurrent neural network.

6. The computer-implemented method of claim 1, wherein the cooking process includes a list of actions to be performed using the matching plant-based source ingredients.

7. The computer-implemented method of claim 1, further comprising:
representing each source ingredient of the plurality of plant-based source ingredients in a D-dimensional space based on the respective set of data features identified for the source ingredient, the representation of the source ingredient in the D-dimensional space comprising at least one of: physiochemical, nutritional, or molecular descriptors of the source ingredient.

8. The computer-implemented method of claim 1, further comprising:
determining a formula and a corresponding similarity score, wherein the formula combines the-matching plant-based source ingredients in specific proportions and the similarity score indicates how similar the formula is to the animal-based target food item in the feature space, wherein determining the formula includes executing an optimization process to determine the specific proportions for combining the matching plant-based source ingredients in the formula using least absolute shrinkage and selection operator (Lasso) regression.

9. The computer-implemented method of claim 1, wherein the training set is created by:
obtaining a set of existing recipes, each existing recipe comprising a respective list of ingredients, respective quantities and respective instructions for cooking the respective list of ingredients; and
obtaining the set of processed existing recipes based on modifying each of the existing recipes, in the set of existing recipes, to include respective atomic directions for cooking the respective list of ingredients of the existing recipe.

10. One or more non-transitory computer-readable storage media storing one or more instructions programmed for generating a recipe using plant-based ingredients to mimic a given animal-based food item, when executed by one or more computing devices, cause:
receiving matching plant-based source ingredients from a plurality of plant-based source ingredients that match an animal-based target food item in a feature space of the plurality of plant-based source ingredients;
applying a machine learning generator model to the at least the matching plant-based source ingredients to generate a recipe that uses the matching plant-based source ingredients to mimic the animal-based target food item, the recipe comprising a cooking process,
wherein the machine learning generator model is trained using a training set, the training set comprising a set of processed existing recipes stored in an existing recipes database, each existing recipe in the set of processed existing recipes including a list of ingredients and a list of instructions for cooking the ingredients in the list of ingredients.

11. The one or more non-transitory computer-readable storage media of claim 10, wherein the one or more instructions, when executed by the one or more computing devices, further cause:
retrieving, from a target database, a set of data features associated with the animal-based target food item, the set of data features for the animal-based target food item comprising at least one of:
physiochemical data features of the animal-based target food item,
nutritional data features of the animal-based target food item, or
molecular data features of the animal-based target food item;
retrieving, from a source ingredients database, a respective set of data features for each of the plurality of plant-based source ingredients, the respective set of data features for each of the plant-based source ingredients comprising at least one of:
physiochemical data features of the plant-based source ingredient,
nutritional data features of the plant-based source ingredient, or
molecular data features of the plant-based source ingredient;
creating a different training set from the respective set of data features for each of the plurality of plant-based source ingredients;
training a machine learning prediction model by using the different training set to generate the feature space of the plurality of plant-based source ingredients.

12. The one or more non-transitory computer-readable storage media of claim 11, wherein the one or more instructions, when executed by the one or more computing devices, further cause:
executing a computer-implemented feature compression method on the respective set of data features for each of the plurality of plant-based source ingredients, to determine a compact representation of the respective set of data features for each of the plurality of plant-based source ingredients, wherein the different training set comprises the compact representation of the respective set of data features for each of the plurality of plant-based source ingredients.

13. The one or more non-transitory computer-readable storage media of claim 11, wherein the set of data features associated with the animal-based target food item and the respective set of data features for each of the plurality of plant-based source ingredients are each associated with a same set of data feature types, and wherein the same set of data feature types comprises at least one of:

a nutritional descriptor feature type,
a physiochemical descriptor feature type, or
a molecular descriptor feature type.

14. The one or more non-transitory computer-readable storage media of claim 11, wherein the machine learning prediction model is based on gradient boosting trees, and wherein the machine learning generation model is based on a recurrent neural network.

15. The one or more non-transitory computer-readable storage media of claim 10, wherein the cooking process includes a list of actions to be performed using the matching plant-based source ingredients.

16. The one or more non-transitory computer-readable storage media of claim 10, wherein the one or more instructions, when executed by the one or more computing devices, further cause:
representing each source ingredient of the plurality of plant-based source ingredients in a D-dimensional space based on the respective set of data features identified for the source ingredient, the representation of the source ingredient in the D-dimensional space comprising at least one of: physiochemical, nutritional, or molecular descriptors of the source ingredient.

17. The one or more non-transitory computer-readable storage media of claim 10, wherein the one or more instructions, when executed by the one or more computing devices, further cause:
determining a formula and a corresponding similarity score, wherein the formula combines the-matching plant-based source ingredients in specific proportions and the similarity score indicates how similar the formula is to the animal-based target food item in the feature space, wherein determining the formula includes executing an optimization process to determine the specific proportions for combining the matching plant-based source ingredients in the formula using least absolute shrinkage and selection operator (Lasso) regression.

18. The one or more non-transitory computer-readable storage media of claim 10, wherein the training set is created by:
obtaining a set of existing recipes, each existing recipe comprising a respective list of ingredients, respective quantities and respective instructions for cooking the respective list of ingredients; and
obtaining the set of processed existing recipes based on modifying each of the existing recipes, in the set of existing recipes, to include respective atomic directions for cooking the respective list of ingredients of the existing recipe.

19. A computing system comprising:
one or more computer systems comprising one or more hardware processors and storage media; and
instructions stored in the storage media and which, when executed by the computing system, cause the computing system to perform:
receiving matching plant-based source ingredients from a plurality of plant-based source ingredients that match an animal-based target food item in a feature space of the plurality of plant-based source ingredients, wherein the feature space is generated by a machine learning prediction model;
applying a machine learning generator model to the at least the matching plant-based source ingredients to generate a recipe that uses the matching plant-based source ingredients to mimic the animal-based target food item, the recipe comprising a cooking process, wherein the machine learning generator model is trained using a training set, the training set comprising a set of processed existing recipes stored in an existing recipes database, each existing recipe in the set of processed existing recipes including a list of ingredients and a list of instructions for cooking the ingredients in the list of ingredients.

20. The computing system of claim 19, wherein each of the plurality of plant-based source ingredients is represented in a D-dimensional space based on their respective set of features comprising at least one of physiochemical descriptors, nutritional descriptors, or molecular descriptors.

* * * * *